United States Patent [19]

Schalkowsky et al.

[11] Patent Number: 4,517,292

[45] Date of Patent: May 14, 1985

[54] METHOD AND APPARATUS FOR TESTING MICROBIAL INTERACTION WITH GROWTH AFFECTING SUBSTANCES

[75] Inventors: Samuel Schalkowsky, Chevy Chase; William Pepper, Jr., Bethesda, both of Md.

[73] Assignee: Spiral System Instruments, Inc., Bethesda, Md.

[21] Appl. No.: 379,367

[22] Filed: May 18, 1982

[51] Int. Cl.³ .................... C12Q 1/18; C12Q 1/24; C12M 1/26; C12M 1/32
[52] U.S. Cl. .................................... 435/32; 435/30; 435/292; 435/293; 435/808
[58] Field of Search ............. 435/6, 7, 29, 30, 32, 435/172, 292, 293, 808

[56] References Cited

U.S. PATENT DOCUMENTS

| | | | |
|---|---|---|---|
| 3,799,844 | 3/1974 | Campbell et al. | 435/30 |
| 3,892,632 | 7/1975 | Campbell et al. | 435/30 |
| 3,962,040 | 6/1976 | Campbell et al. | 435/30 |
| 4,352,880 | 10/1982 | Awerbuch | 435/6 |
| 4,353,988 | 10/1982 | Couse et al. | 435/287 |

FOREIGN PATENT DOCUMENTS 1455953 11/1976 United Kingdom .............. 435/293

OTHER PUBLICATIONS

DeFlora S., "A Spiral Test Applied to Bacterial Mutagenesis Assays", Mutation Research, vol. 82 (Jul. 1981), pp. 213–227.
User Manual: Model 500A Laser Bacteria Colony Counter, Oct. 1981, Spiral Systems Instruments, Inc., Bethesda, Md.
Schalkowsky et al., "Application of the Spiral Plating Method to Bacterial Interaction Tests" Poster Presentation at 3rd International Symposium on Rapid Methods and Automation in Microbiology, 5/27/81, Washington, D.C.

Primary Examiner—Sidney Marantz
Assistant Examiner—Randall E. Deck
Attorney, Agent, or Firm—Antonelli, Terry & Wands

[57] ABSTRACT

A method and apparatus for calculating the growth interacting substance potency and growth ratio for the intersections of a scanning spot with a track of visible microbial colonies on an interaction plate. The potency is a measure of the weight of a growth interacting substance which is deposited on the interaction plate per unit volume of the growth culture medium. The growth ratio is a measure of the growth interacting substance effect on growth of colonies of microbes on the interaction plate along the path of interaction of the scanning spot with visible microbial colonies.

22 Claims, 7 Drawing Figures

METHOD AND APPARATUS FOR TESTING MICROBIAL INTERACTION WITH GROWTH AFFECTING SUBSTANCES

CROSS REFERENCE TO RELATED APPLICATION

Reference is made to application Ser. No. 379,281 entitled Method for Testing Microbial Interaction with Growth Affecting Substances which names Samuel Schalkowsky and Ellen Schalkowsky as inventors and filed on even data herewith.

BACKGROUND OF THE INVENTION

1. Field of the Invention

The invention relates to methods for measuring the effect of growth interacting substances on microbial growth.

2. Description of the Prior Art

One well known test is the spot diffusion test in which a solution of a growth interacting substance is applied to a culture medium which has been inoculated with microbes. The resultant plate is incubated for a period of time sufficient to produce visible microbial colonies for areas of the plate where the potency of the growth interacting substance was not high enough to inhibit growth. The spot test has known deficiencies. First, it does not provide direct quantitive identification of the potency of the growth interacting substance at points of interest on the incubated plate such as the point of inhibition. Second it is limited by the degree of diffusibility of growth interacting substances into the microbial culture medium.

A second well known testing method of growth interacting substances involves the making of a series of solutions of increasing dilution of the growth interacting substance. Each solution is applied to a microbial culturing medium which has been inoculated with a microbe solution and incubated for a time sufficient to detect the effect of the solution on microbial growth. This method also suffers from known drawbacks. In the first place, it requires time consuming manual dilutions and requires the use of a large number of culture media containers. It also does not readily yield precise quantitative data on the potency of the growth interacting substance being studied. In the case of its use to detect the point of inhibition, it usually reveals only a range of potency between which growth inhibition occurs.

The spot and the dilution tests both suffer from the drawback of not readily facilitating testing of growth interacting substances to determine their effects in potencies which are less than those which completely inhibit microbe growth.

The dilution method is also used to determine the effect of growth interacting substances at less than inhibiting potencies by counting the number of surviving microbial colonies. The disadvantage of this procedure is that it requires separate tests since exposure times for survivor measurements are generally different than exposure times for inhibition measurement.

All of the above methods suffer from being time consuming because of the need for manual manipulation and because they do not readily yield continuous quantitive information on the potency of a growth interacting substance for diverse points of interest on a growth curve of the microbes being studied.

Spiral Systems, Inc. manufactures an instrument under the trademark SPIRAL PLATER for plating onto a microbial culture medium a solution containing an unknown concentration of microbes to determine the concentration of microbes in the solution by counting the resultant colonies after an incubation period. The solution is deposited on a circular culture medium plate in an Archimedes spiral. The solution decreases in volume per unit length of the spiral as the radius of the spiral increases. The apparatus is described in U.S. Pat. Nos. 3,799,844, 3,892,632, and 3,962,040. These patents are incorporated herein by reference.

A laser bacteria colony counter (Model 500A) is manufactured by Exotech Incorporated, of Gaithersburg, Md., specifically for counting the colonies which result from the plating of a microbe containing solution with the SPIRAL PLATER. The laser counter is the preferred microbe colony scanning mechanism which is used with the invention. The Model 500A is described in a brochure entitled "User Manual Model 500A Laser Bacteria Colony Counter, October 1981" by Spiral System Instruments, Inc. of Bethesda, Md., 20814. The description of the Model 500A is incorporated herein by reference.

The Food and Drug Administration pursuant to 21 CFR 036.105 requires that each manufacturer of antibiotics must run tests of each batch of newly manufactured antibiotic to determine compliance with potency standards. Implementation of this requirement entails the measurement of zones of inhibition of the test substance relative to the size of inhibition zones produced by known potencies of control substances. Measurement of these zones of inhibition is done either manually or by vidicon scanners. These tests are costly in their need for extensive time, materials, and equipment.

DEFINITIONS

1. Growth Interacting Substance—Any substance deposited in a programmed concentration on a culture medium which either inhibits or induces growth of microbes. Substances which inhibit growth of microbes are referred to as growth inhibiting interacting substances and substances which induce growth are referred to as growth enhancing interacting substances.

2. Control Plate—A plate containing a culture medium on which a track of microbes has been deposited and incubated for a period of time sufficient to produce visible colonies along the track to provide a reference track width for growth measurement in the absence of a growth interacting substance.

3. Interaction Plate—A plate containing a culture medium on which are deposited (1) microbes in the same track configuration and concentration as the control plate, and (2) a growth interacting substance in contact with the microbes. The plate is incubated for a period of time sufficient to produce visible colonies along at least part of the track.

4. Concentration—The number of microbes per unit volume contained in a liquid suspension which is deposited on the interaction and control plates to produce the visible colonies of microbes.

5. Potency (Pi)—The weight of the growth interacting substance which is deposited on the interaction plate per unit volume of the growth culture medium.

6. Line of Intersection—The path followed by the spot of a scanner during the intersection of the spot with a track of visible microbial colonies on the interaction plate.

7. Length of Interception (Li)—The length that the spot of a scanner intercepts visible microbial colonies along the line of intersection of the spot with a track of visible microbial colonies. For continuous microbial colonies, the length of interception is the length of the line of intersection of the spot with the track. For discontinuous microbe colonies, the length of interception is the sum of the separate intercepted line segments of the spot with discrete colonies along the line of intersection. The length of interception is a measure of the number of microbial colonies and their size. The size of a colony is a measure of the number of bacteria in the colony and hence a measure of bacterial growth rate.

8. Track Width (Wi)—The average width of a track of continuous (WC) or discontinuous (WD) microbial growth on the interaction plate along the line of intersection of the spot with the track. The width (Wi) is defined by the equation $Wi = Li \times \Delta R / 2 T_i R_i$ where $R_i$ is the average radius of the spot measured from the center of the spiral, along the line of intersection of the spot with the visible microbial colonies; $\Delta R$ is the radial distance between adjacent spirals of the microbial track, and Li is the length of interception. The discontinuous track width WD is less than the distance between the largest separation of visible colonies on opposite edges of the track of visible colonies.

9. Reference Width (Wo)—The width used in computing the growth ratio GRi. The reference width may be that measured from a control plate, it may be the largest value of Wi measured on the interaction plate or it may be an arbitrarily assigned value, e.g. Wo=1.

10. Growth Ratio (GRi)—The ratio of track width Wi and the reference width Wo.

11. Local Growth Measurement (LGM)—The measurement of track width Wi made during a single revolution of the scanner.

12. Regional Growth Measurement—The average value of a number of contiguous local growth measurements.

13. Growth Curve—The relationship of growth ratio, GRi, and Potency, Pi, for a particular combination of growth interacting substance and microbial population. A growth curve may be based either on local or regional growth measurement and is derived from those portions of the interaction plate for which there is measurable microbial growth.

SUMMARY OF THE INVENTION

The invention is methods and an apparatus for determining the effects of a growth interacting substance on microbial growth by utilizing an interaction plate. The interaction plate contains visible microbial colonies produced by the programmed deposition of a microbe containing solution on a track on the plate, the programmed deposition of a growth interacting substance on the interaction plate in contact with the microbes and incubating the plate. In the first embodiment of the invention, a point of interest along the microbial track on an interaction plate, such as the point at which microbial growth is first completely inhibited, is identified and the corresponding potency of the growth interacting substance is precisely determined from the known program of the deposition of the growth interacting substance. The second embodiment of the invention is based upon the discovery that the width of the track on the interaction plate of any point of interest may be measured and compared with a reference width to produce a measurement of the effect of the growth interacting substance on microbial growth. The second embodiment of the invention preferrably uses control and interaction plates in which each track is a spiral, the interaction plate has a gradient of deposition of the growth interacting substance which decreases in volume per unit length as the radius of the spiral track increases an the microbe containing solution concentration is constant per unit length of the track on the control and interaction plates. The potency of the growth interacting substance at any point on the track of visible microbial colonies may be calculated by use of published figures of the known program deposition characteristics of the apparatus which applies the growth interacting substance to the interaction plate. The growth ratio and potency of the growth interacting substance may be analyzed for each line of intersection of the scanning spot with the track of visible microbial colonies.

A growth curve of the growth ratio versus potency of each growth interacting substance may be made. The growth curve may be analyzed to quantitate selected growth curve information of interest such as slope, maximum, minimum, or intercepts with the GRi=0 axis, etc.

The first embodiment of the invention is a method for investigating the effect of a growth interacting substance on microbial growth by determining the potency of the growth interacting substance at a point of interest within visible colonies present on an incubated growth interaction plate. The method includes the steps of applying a pattern of a microbe containing solution in a pattern on an interaction plate; applying a solution of the growth interacting substance on the interaction plate in a programmed potency in contact with the microbes; incubating the interaction plate for a time sufficient to produce visible microbial colonies on the interaction plate; and determining the potency of the growth interacting substance at the point of interest by correlating the position of the point of interest within the visible colonies with the programmed volume per unit length of the growth interacting substance deposited at that point. In the preferred form of the method, the patterns are Archimedes spirals; the potency of the growth interacting substance is a gradient which changes with the radius of the pattern; and the concentration of the microbe containing solution is constant per unit length of the spiral.

The method of the second embodiment of the invention includes the steps of scanning an interaction plate with a scanner which scans a spot in a series of adjacent paths to detect a length of interception of the spot with visible colonies of microbes within a track along a line of intersection of the spot with the track; calculating the average width of the track of visible microbe colonies along the line of intersection of the spot with the track from the detected length of interception of colonies which is a measure of the number of microbial colonies and their size; calculating the growth interacting substance potency at each line of intersection of the spot with the track of visible colonies; and calculating the growth ratio for each intersection of the spot with the track of visible colonies by calculating the ratio of track width for the line of intersection of the spot with the interaction plate divided by a reference width.

An apparatus in accordance with the second embodiment invention includes scanning means for scanning a spot in a series of adjacent lines for detecting the visible colonies of microbes along a line of intersection of the spot with the track of visible microbes; means responsive to the scanning means for detecting a length of interception of the spot with the visible colonies of microbes along the line of intersection of the track of visible colonies which is a measure of the number of microbial colonies and their size; means responsive to the scanning means for calculating the average width of the track of visible microbial colonies for each line scanned by the scanning means; means for calculating the growth interacting substance potency at each line of intersection of the spot with the track of visible colonies; and means for calculating the growth ratio for each line of intersection of the spot with the track of visible colonies by computing the ratio of track width for the line of intersection of the spot with the track of visible colonies and a reference width.

The invention had advantages over the prior art methods and apparatus. A continuous measure of the interaction effects of growth interacting substances on microbial growth is produced. The continuous measure of the growth interaction effect enables identification of discrete points of interest anywhere on the growth curve of any growth interacting substance. Moreover, the precise detection of the point where microbial growth is inhibited by the growth inhibiting substance is facilitated. The study of the growth interaction effects on microbial growth is facilitated at potencies where microbial growth is not totally inhibited. The effects of a growth interacting substance on microbial growth may be studied over a wide range of potencies with a single plate.

DESCRIPTION OF THE PREFERRED EMBODIMENTS

Figure 1A:
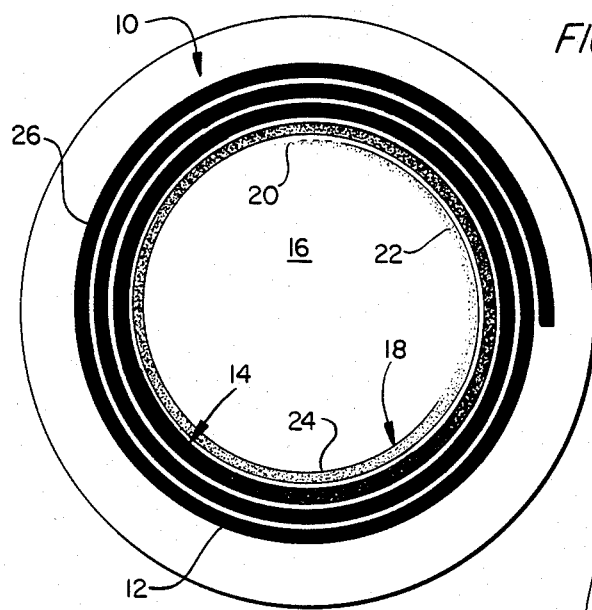
FIG. 1A is an illustration of an interaction plate used with the invention.

FIG. 1A illustrates an interaction plate 10 having visible microbial colonies 12 in a growth pattern 14 in the form of a spiral. The interaction plate of FIG. 1A is representative of the interaction plate used when the invention is used to study growth inhibiting interacting substances in which the highest potency is applied near the center of the plate. It should be understood that the particular form of microbial growth pattern will vary with the gradient of the deposition of the growth interacting substance and the microbe containing solution and whether the particular growth interacting substance is a growth inhibiting or a growth enhancing substance or a combination of both. The invention may be used with different forms of interaction plates other than the one used in FIG. 1A. The interaction plate 10 is made by pouring a solution of agar into a petri dish in accordance with known methods. The interaction plate 10 normally has the visible colonies in a partial spiral track 14. The plate has an inner circular area 16 in which no visible colonies appear because the growth interacting substance was applied with a potency which inhibited all growth. The plate 10 also has an area of discontinuous microbial colony growth 18 which includes an area 20 where all visible microbial colony growth approaches zero (inhibition point), an area 22 where the visible microbial colonies are discrete but of higher density, and an area 24 where the number of colonies while still being discontinuous is denser than area 22 with the greatest number of colonies appearing near the inside and outside boundaries of the spiral track 14 and the interior of the track having fewer visible colonies. The plate 10 also has an area of continuous microbial colony growth 26 where the number of colonies appears so dense that the colonies run together so that discrete colonies are no longer visible.

The interaction plate 10 of FIG. 1A is preferably made by using a commercially available instrument manufactured by Spiral Systems, Inc. and marketed under the trademark SPIRAL PLATER to deposit an Archimedes spiral of a microbial solution in a constant concentration per unit length of the track 14 and to deposit a solution of the growth interacting substance in a programmed gradient which decreases with increasing radius in contact with the microbes in the same Archimedes spiral as the microbial solution. The resultant interaction plate 10 is incubated for a period sufficient for visible microbial colonies to appear. The instrument is disclosed in U.S. Pat. Nos. 3,799,844, 3,892,632, and 3,962,040. The instrument can be purchased with constant and variable cams which function as programs for respectively applying the test solution at a constant volume per unit length of the track 14 and with a gradient which varies in volume per unit length of the track 14. With the variable cam, the programmed gradient varies from the center of the plate 10 to its circumference in a ratio of about 40:1 for standard 10 cm plates and 600:1 for standard 15 cm plates. The potency of the growth interacting substance and concentration of microbes at any point on the track 14 may be calculated from the known programmed gradient of deposition and published information provided by Spiral System Instruments, Inc. One source of the published information is a paper entitled "Application of the Spiral Plating Method to Bacterial Interaction Tests" by Samuel and Ellen Schalkowsky, which was presented on May 27, 1981 at the 3rd International Symposium on Rapid Methods and Automation In Microbiology and which is incorporated herein by reference in its entirety. Appendix A of the paper may be used to calculate the potency of the growth interacting substance at any point on the spiral track 14 of a standard 10 cm plate. The information in the aforementioned appendix correlates the radius of the point on the spiral track 14 on which potency information is needed with the number of microliters per millimeter squared deposited at that location by the SPIRAL PLATER. It should be understood that the invention is not limited to the use of the SPIRAL PLATER and is not limited to the use of the commercially available programs for producing potency gradients.

An important physical characteristic of the interaction plate 10 is that the width of the track 14 of visible microbial colonies decreases as the potency of the growth interacting substance increases. In FIG. 1A, where the potency of the growth interacting substance was applied in a spiral track beginning near the center of the plate with an exponentially decreasing gradient, the width of the track 14 of visible microbial colonies 12 increases inversely to the potency of the growth interacting substance applied to the spiral track. The invention measures the effect of the growth interacting substance on microbial growth by comparing the ratio of the width of the track 14 at each point of interest with a reference width Wo which may be the width of a track of a control plate.

Figure 1B:
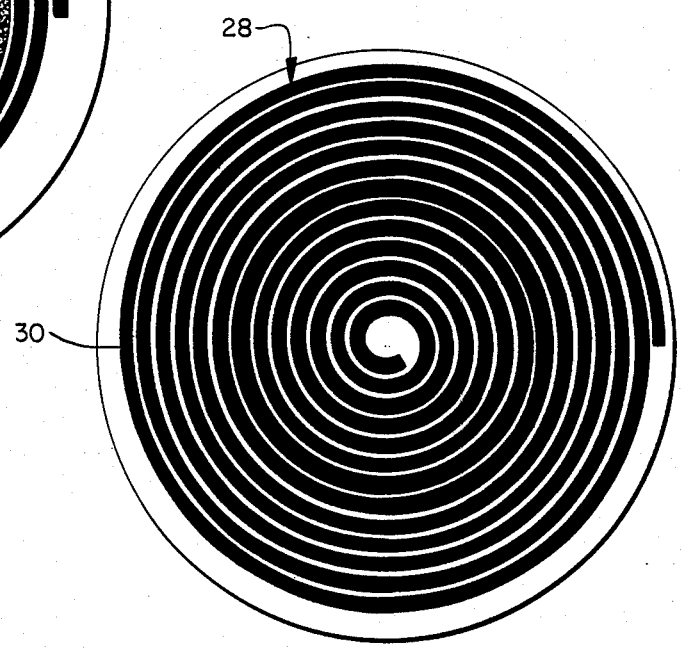
FIG. 1B is an illustration of a control plate used with the invention.

FIG. 1B illustrates the control plate 28 which is used with the interaction plate 10 of FIG. 1A to provide a reference of microbial growth when there is no growth interacting substance present. The control plate 28 is made by applying an Archimedes spiral of a microbe containing solution in a constant concentration per unit length identical to the solution applied to the interaction plate 10 of FIG. 1A. The control plate 28 is incubated to produce continuous microbial colonies 12 in an Archimedes spiral track 30. The width of the spiral track 30 is constant in view of the absence of a growth interacting substance. The width of the track 30 may be measured and stored in memory as a reference width Wo as an input to the apparatus of FIG. 3.

Figure 2:
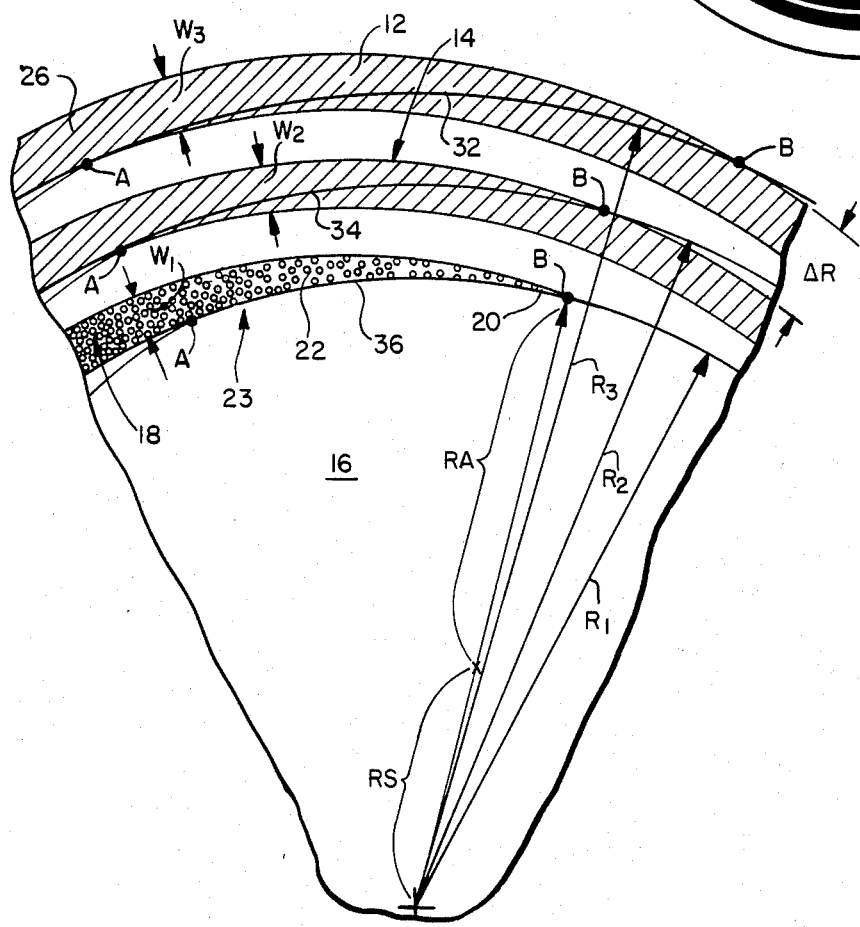
FIG. 2 is an illustration of an expanded section of FIG. 1A illustrating the function of a scanner used with the invention.

FIG. 2 is an expanded view of a section of the interaction plate 10 of FIG. 1A which illustrates the lines intersection 32, 34, and 36 of the scanning spot with the track 14. The inner radial end point of the lines of intersection 32, 34, and 36 is identified by the letter A and the outer radial end point is identified by the letter B. The lines of intersection are the path of the scanner spot (FIG. 3) across the tracks 14 and are of constant radius when a circular spot scanner is used or a slowly varying radius when a spiral spot scanner is used. Either type of scanning path may be used with the apparatus of FIG. 3 with the spiral spot scanner being preferred in view of its commercial availability. When either a circular or a spiral scanner is used, the radius of the scanning spot decreases by a distance $\Delta r$ for each successive revolution of the spot scanner which causes the spot to start at the outside of the plate and scan toward the center. The zone of inhibition 16 is defined by a radius of substantially constant radius, such as radius R1, (line of intersection 36). The reason that the zone of inhibition 16 is substantially circular is that the interacting substance tends to diffuse from the point of application such that the resultant diffusion potency gradient decreases with increasing radius thus causing the locus of points of equal potency to be defined approximately by a circle. FIG. 2 illustrates the increase in widths with increasing radius of the track 14 where $W3 > W2 > W1$ as stated above with reference to FIG. 1.

FIG. 2 illustrates parts of the incubated interaction plate 10 which are important in understanding the present invention. The inhibition tail 23 is the area between points A and B respectively of the innermost visible spiral of deposition. Several measured parameters of the incubated interaction plate of FIG. 2 are used by the apparatus of FIG. 3. The quantity RS is the radius of starting point of the deposition of the growth interacting substance and the microbial-containing solution on the interaction plate. The quantity RA is the distance from the starting radius RS to the point of interest illustrated as the inhibition point B where microbial growth ceases of the innermost visible spiral of deposition. The radius of the spot scanner at any point of interest is equal to the sum of $RS + RA$. The radii $R_1$, $R_2$ and $R_3$ represent different average scan radii of the spot scanner.

Figure 3:
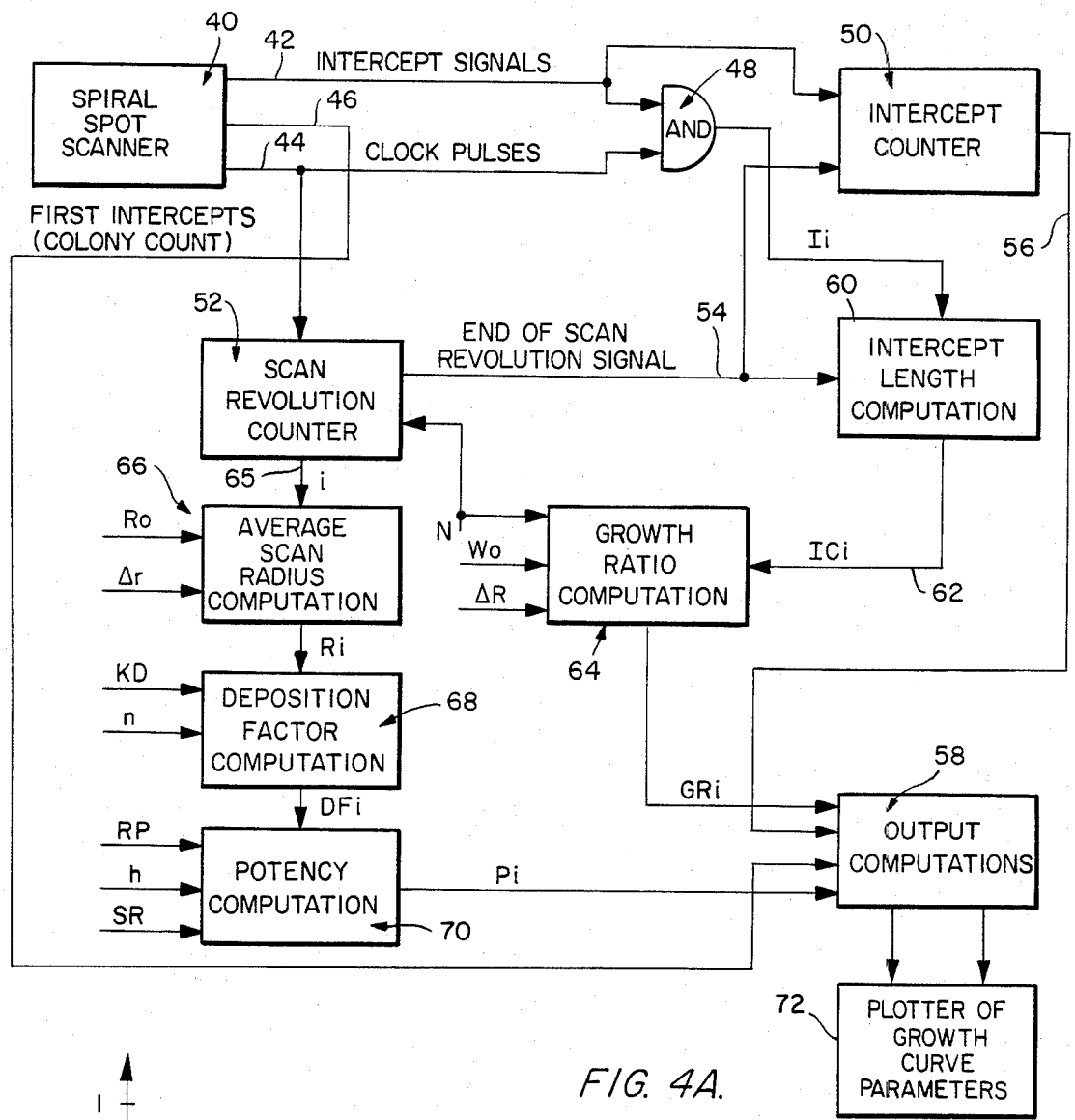
FIG. 3 is a schematic of an apparatus used with the invention.

FIG. 3 illustrates the preferred apparatus of the second embodiment of the invention. A spiral spot scanner 40 is used to scan the interaction plate 10 of FIG. 1A described above. The spiral spot scanner preferrably scans a laser beam in a spiral of decreasing radius over the interaction plate 10 to detect the visible microbial colonies 12 in the track 14. Although a circular spot scanner may be used with the apparatus of FIG. 3, the preferred form of the scanner is a Model 500A spiral spot scanner manufactured by Exotech Incorporated of Gaithersburg, Md., which is referred to in the Description of the Prior Art. The Model 500A has outputs 42, 44, and 46 which, respectively, are signals of each intercept of the spot scanner with each microbial colony 12 (either continuous or discontinuous), the internal clock signal of the scanner, which has 1024 clock pulses per scan revolution, and a signal indicating the detection of previously undetected microbial colonies 12. The intercept output signal on line 42 is connected to an And gate 48. The clock output line 44 is also coupled to the And gate 48. The total number of outputs of the And gate 48 per scan revolution is a function of the length of the line of intersection of the spot during which the spot is intercepting visible microbial colonies. When continuous microbial colonies 12 are being intercepted, such as when scanning along line of intersection 32 of FIG. 2, the length of interception is equal to the length of the line of interception AB. When discontinuous microbe colonies 12 are being intercepted, such as with the scanning along line of intersection 36 of FIG. 2, the length of interception is less than the length of the line of interception AB and is proportional to the density of the microbial colonies along the line of intersection as will be described infra. The length of the line of interception is used to calculate the average width Wi of the track 14 along the line of intersection of the scanning spot. The intercept output 42 is also coupled to intercept counter 50 which functions to count the total number of intercepts during each revolution of the scanning spot of scanner 42. The scanner clock 44 output is also coupled to a scan revolution counter 52 which contains an internal counter which provides an end of scan revolution signal on line 54 when the count total equals the number of clock pulses N per revolution of the scanner 40. When the Exotech Model 500A laser spot scanner is used, the scan revolution internal counter counts to 1024 to signal the completion of a scan revolution. The end of scan revolution signal of line 54 is applied to the intercept counter 50 which has been previously described to synchronize the counting of intercepts with the completion of a scan revolution. The output from the intercept counter 50 on line 56 is connected to the output computation block 58. The total count stored in the intercept counter 50 is monitored by the output computation block 58 to detect when the spot scanner begins scanning in the discontinuous microbial growth area 18 of FIG. 1A. When the scanner is scanning in the continuous microbial colony area 26 of FIG. 1A, the total of the counter 50 stays at a low number such as one or two. When the intercept counter 50 repeatedly totals a number of intercept counts greater than two, it is an indication that the discontinuous area of microbial colony growth is being detected. While the number of the total count of the intercept counter 50 which is chosen to indicate the interception of discontinuous colonies for any one line of intersection is a matter of choice, a suitably programmed microprocessor can monitor the intercept counter output to signal the presence of discontinuous colony growth in accordance with the foregoing analysis. The output of the AND gate 48 is applied to an intercept length computation block 60 which totals the number of pulses outputted by the AND gate 48 during each revolution of the spot of the spot scanner 40. As described supra, the total number of output pulses from AND gate 48 per scan revolution which are totaled by the intercept length computation block 60 is a function of the density of the microbial colonies along the line of intersection. The output of the intercept length computation block 60 ICi is applied on line 62 to the growth ratio computation block 64 which computes the growth ratio GRi for each revolution of the spot scanner in accordance with the relationship $GRi = (\Delta R \times ICi)/(Wo \times N)$ wherein Wo (reference width) is the measured width of the visible microbial colonies on the control plate, N is the number of clock pulses on the output line 44 of the scanner 40 per revolution of the scanner, ICi is the output from the intercept length computation block 60 and $\Delta R$ is the radial advance between successive revolutions of the spiral of the interaction plate 10. The mathematically rigorous definition of $$Wi = \frac{Li \Delta R}{2\pi R_1}$$

is not readily calculable with the system of FIG. 3 because the measurement of the length of interception Li is not directly measurable. The invention calculates $$Wi = \frac{\Delta R \; ICi}{N}$$

from the parameters $\Delta R$, N, and ICi; which are available in the system of FIG. 3 as inputs to the growth computation box 64. As has been explained, supra, the length of interception Li, which is equal to the quantity ICi produced as an output of the length of interception box 60, is a measure of both the number and size of bacterial colonies. Determination of colony size and number is an important measure of the effectiveness of a growth interacting substance. The quantity GRi is an indication of the effectiveness of the potency of the growth interaction substance in affecting growth on the interaction plate 10 along the ith scan of the spot scanner. A GRi of 1 indicates no growth effect; a $GRi > 1$ indicates an enhancement of growth; a $GRi < 1$ indicates an inhibitory effect and a GRi of near or at zero indicates the point of inhibition 20 of FIG. 2.

The potency computation Pi is made by utilizing known information from the programmed gradient deposition of the growth interacting substance referred to as supra. The average scan radius Ri of each revolution of the spot scanner during intersection of the spot with the track 14 of visible colonies N on the interaction plate is computed by the average scan radius computation block 66 which solves the equation $Ri = (Ro - \frac{1}{2}\Delta r) - i \times \Delta r$ wherein Ro is the initial scan radius of the spot scanner, i is the number of the revolution of the scanner with there being 500 revolutions per plate and is the output from the scan revolution counter 52 on line 65 and $\Delta r$ is the spiral advance between adjacent revolutions of the scanner. The deposition factor DFi for each line of intersection i of the spot with the visible colonies 12 on the track 14 is determined by the deposition factor computation block 68. This determination can be made from use of information such as that in the appendix A, provided by Spiral System Instruments, Inc., of deposition factor values as a function of position along the spiral track for the particular SPIRAL PLATER model being used. Alternately, it can be computed from an equation applicable to the SPIRAL PLATER being used. For example, for the Model C SPIRAL PLATER in the 40 microliter deposition mode, the deposition factor DFi can be computed from the equation $DFi = [KD/(RA+12)] \times 10 \, EXP(-n \times RA)$ microliters per millimeter squared, where $KD = 0.5746$, $n = 0.039$, and RA is the distance from the deposition starting radius to the radial position of the point of interest on the spiral track. The potency Pi is calculated in response to the deposition factor computation DFi by the potency computation block 70 which solves the equation $Pi = (RP \times DFi)/h \times SR)$ wherein h is the height of the culture medium in the interaction plate 10, RP is the reference potency used in depositing the growth interacting substance in micrograms per ml and SR is a correction factor to account for less than complete diffusion or spreading between adjacent turns of the track 14 when less than a continuous gradient exists between adjacent turns. The SR correction factor is the fraction of the spiral track separation $\Delta R$ which is covered by the growth interacting substance.

The value of SR can be measured by making two plates. In the first plate, the sample is deposited directly over the spiral pattern while, in the second plate, the growth interacting substance is deposited in between the tracks of the spiral pattern (by rotating the turntable 180° relative to the starting position of the first plate). If there is significant displacement of a point of interest on the inhibition tail 23 such as the point of inhibition B at radius $R_1$ in FIG. 2 for the respective plates, the ratio of the corresponding value of DF(i) will give a quantitative value of SR.

The output computations performed by the output computation block 58 involve data analysis of the potency and growth ratio computations performed by the growth ratio block 64 and the potency computation block 70. As described supra, the point where the microbe colony growth changes from continuous to discontinuous growth is detected by monitoring the count of the intercept counter 50. The point of inhibition may be detected by monitoring the output line 46 of the spiral spot scanner to detect when no new visible microbe colonies have been detected after a given number of revolutions of the spot scanner 40. The number of revolutions which must be completed without detecting a new colony to signal an indication of the point of inhibition is a matter of choice. The actual implementation of the detection of the point of inhibition 20 may be accomplished by a suitably programmed microprocessor. The computation performed by the output computation block 58 may also be either local growth measurements LGM for a single line of intersection of the spot with the visible microbe colonies 12 of the spiral track 14 or a regional growth measurement RGM which is the average value of a number of contiguous local growth measurements. The computation performed by the output computation block 58 may also involve the detection of points of limitation e.g. maximum or minimum and slopes of the type illustrated in FIGS. 4A, 4B, and 4C discussed infra. The outputs of the output computations block are applied to a plotter 72 which produces the curves of FIGS. 4A-4C.

It is important to assure alignment of the center of the interaction plate and the center of the scan radius. One way of detecting if proper alignment exists is to monitor the growth ratio GR versus potency P curve from the output of the computation block 58 for the presence of a periodic component which is indicative of misalignment. For example, such a periodic component would manifest itself in the growth ratio GR versus potency P curve of FIG. 4A as a periodic component in the line segment SCI. The detection of a periodic component can be visually observed or signalled. The operator would then be aware that alignment correction was required and would take appropriate steps to check the placement of the interaction plate on the scanner. If this procedure does not eliminate the misalignment, a recalibration of the alignment of the SPIRAL PLATER and the scanner 40 should be performed.

Figure 4A:
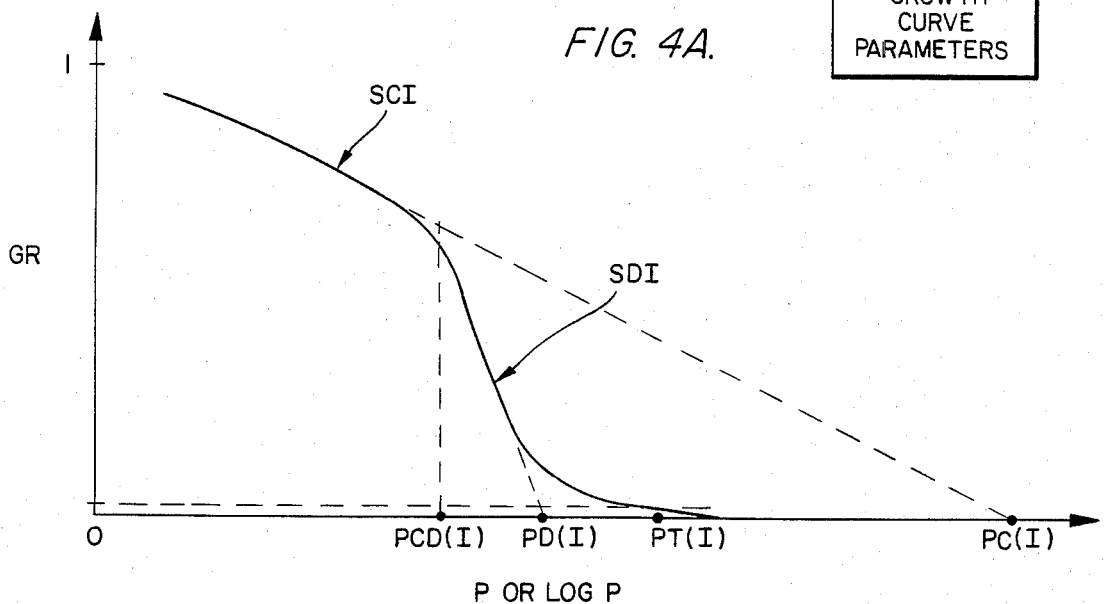
FIG. 4A is an illustration of a growth curve for a growth inhibiting interacting substance obtained with the apparatus of FIG. 3.

FIG. 4A illustrates the growth curve which is typically obtained by use of the invention to analyze interaction plates for growth inhibiting interacting substances such as biocides or antibiotics. The growth curve has essentially three distinct regions. The area SCI represents the continuous growth region of the visible colonies of microbes. The area SDI represents the discontinuous growth region of the visible colonies of microbes. The point PT(I) represents the point of inhibition which may be chosen to represent a GR value of zero or approaching zero. The potency PCD(I) represents the transition between continuous and discontinuous microbial growth. The potency PD(I) represents an extrapolation of the linear discontinuous region of microbial colony growth to zero growth ratio. As the potency of the growth interacting substance continues to increase, the linear slope SDI gives away and rolls off toward zero. The potency PC(I) represents a linear extrapolation of the SCI continuous growth region.

Figure 4B:
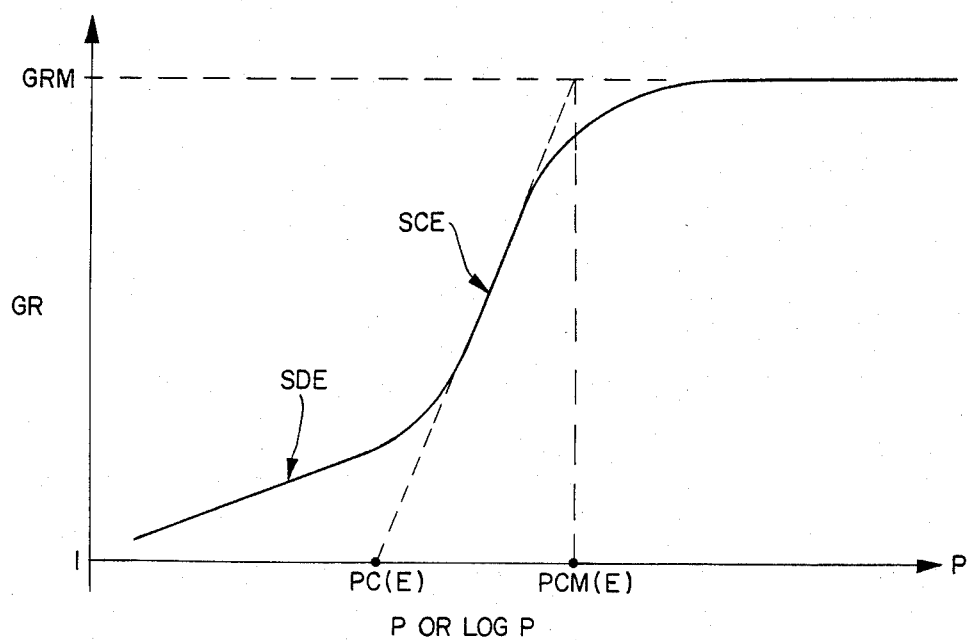
FIG. 4B is an illustration of a growth curve for a growth enhancing interacting substance obtained with the apparatus of FIG. 3.

FIG. 4B illustrates the growth curve which is typically obtained by use of the invention to analyze interaction plates for growth enhancing interacting substances such as vitamins. Like FIG. 4A, the growth curve is comprised of essentially three segments. The first segment SDE represents the region of low density visible microbial colonies where there is a slight enhancement of microbial growth as represented by a growth ratio larger than one. The next region SCE represents an area where there is a sharp linear increase in growth ratio as a function of increasing potency. In this region the microbial colony growth becomes more dense. The potency PC(E) represents an extrapolated potency of the SCE region. Finally, as the potency increases past PCM(E) the growth ratio approaches a maximum GRM.

Figure 4C:
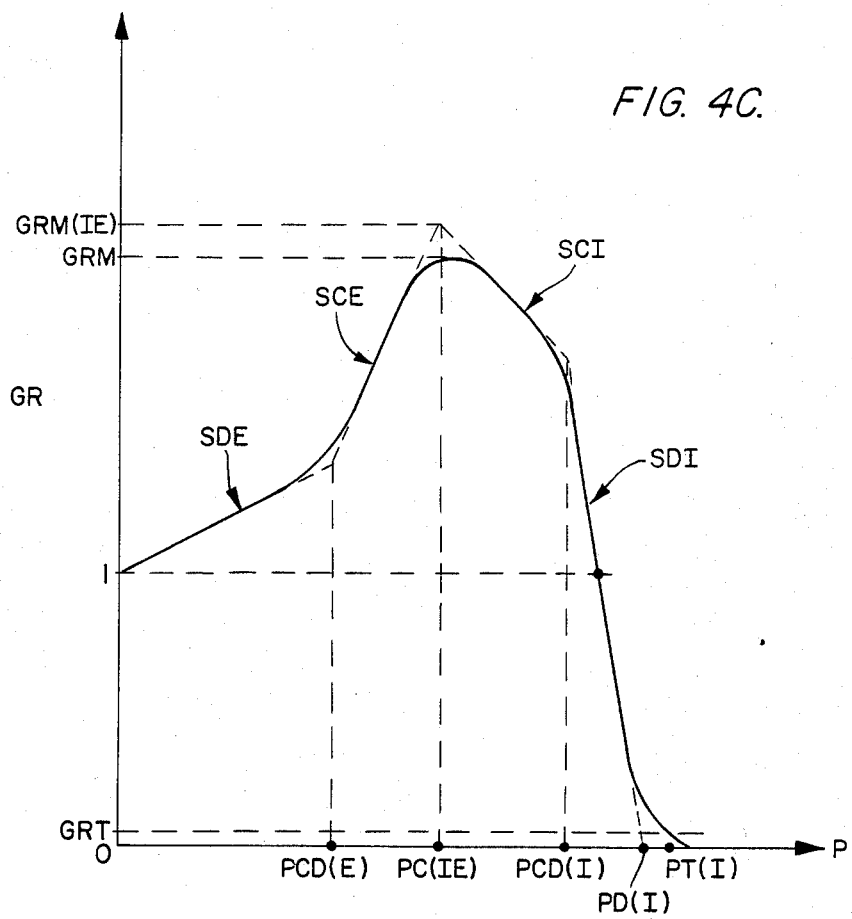
FIG. 4C is an illustration of a growth curve for a substance which exhibits both growth inducing and growth inhibiting properties, obtained with the apparatus of FIG. 3.

FIG. 4C illustrates the growth curve which is typically obtained by use of the invention to analyze interaction plates for mutagenic growth interacting substances. As is apparent from inspection of FIG. 4C, a mutagen can have both growth enhancing and inhibiting characteristics which vary as a function of potency. The region SDE represents a region of linear enhancement of growth by the mutagenic substance. The growth curve changes slope at potency PCD(E) to a region SCE of more sharply enhanced growth. The maximum growth ratio is represented by the reference GPM which occurs at a potency PC(IE). As the potency continues to increase, the mutagenic substance becomes inhibitory in region SCI. The inhibition in region SCI falls off with increasing potency until the potency PCD(I) is reached where the inhibitory effect becomes more pronounced in region SDI where the growth ratio falls off sharply until it approaches zero at potency PT(I). Potency PD(I) is the potency represented by the extrapolation of region SDI to a growth ratio of zero. The growth ratio GRM(IE) represents an extrapolation of the SCE and SCI regions.

FIGS. 4A-4C represent a wide range of typical growth curves which may be obtained by use of the invention to analyze interaction plates. With the invention the foregoing types of curves may be obtained directly from plotting the information available at the output computations block 58 of FIG. 3.

It should be understood that the schematic illustrated in FIG. 3 is intended to illustrate the functions to be performed by the invention. In the preferred form of the invention, the calculations performed by the various computation devices of FIG. 3 would be made by a suitably programmed microprocessor which would perform each requisite calculation task serially in a single computation loop. The programming of a microprocessor to perform the computation tasks of FIG. 3 does not constitute part of the invention and is routinely accomplished by a computer programmer.

It should be understood that while the preferred form of the invention uses spiral patterns for the deposition of the growth interacting and microbe containing solutions, and for scanning the incubated plate other deposition and/or scanning patterns may be used without departing from the spirit and scope of the invention. Also, while reference is made herein to a spot scanner, it should be understood that the invention may be used in conjunction with multiple spots used to scan simultaneously. Accordingly, the term "spot", as used in the specification and in the claims, covers either a single spot or multiple scot scanner.

The following example illustrates the use of the method of the first embodiment of the invention.

EXAMPLE

A suspension of *B. Subtilus* VAR Niger spores in a concentration of about one million per ml was deposited at a uniform rate on a 10 cm petri dish containing 20 ml of Mueller Hinton agar with a Spiral Systems, Inc. SPIRAL PLATER Model C with the spacing between spirals set to be 3.1 mm. Then a Streptomycin solution of 400 mg/ML was deposited on top of the bacterial spiral pattern. The resultant plate was incubated for approximately 20 hours which produced a partial spiral of visible colonies including both a contiguous growth section and a discontinuous growth section. The radius of the point of inhibition was located and measured at approximately 11 mm. The measured radius of 11 mm was used to compute the average concentration of Streptomycin in the column of agar below the point of inhibition of about 1.1 micrograms per ml by using published data pertaining to the model of the SPIRAL PLATER used. This value was used to represent the minimum inhibitory concentration of Streptomycin acting on the microbes in the tested concentration.

The foregoing example is illustrative of the method of the first embodiment of the invention. The first embodiment of the invention is applicable to determining the point of inhibition of other microbes in combination with other growth interacting substances. The first embodiment may also be used to determine the potency of the growth interacting substance for any point of interest within the visible microbial colonies on an interaction plate. Thus, with reference to FIG. 1A, the potency Pi of the growth interacting substance at the point of inhibition 20 is determined by measuring the radius between the center of the interaction plate and point 20 and correlating the measured radius with the published figures referred to supra. Specifically, as set forth, supra, the equation $Pi = (RP \times DFi)/(h \times SR)$ is solved for each point of interest. The deposition factor DFi is obtained from Appendix "A" of the aforementioned paper for the radial distance RA between the starting radius of the spiral track to the point of interest. The factor SR is obtained as set forth above and h is the thickness of the culture medium in the interaction plate. Similarly, the potency at other points of interest of the growth interacting substance is determined by measuring the radius between these points and performing the aforementioned correlation of the point of interest with the published data.

What we claim is:

1. A method for determining the effect of a growth interacting substance on microbial growth by utilizing an interaction plate which contains visible microbial colonies in a track produced by the programmed deposition of a microbe containing solution on a track on the plate and the programmed deposition of a track of a growth interacting substance on the interaction plate in contact with the microbes and incubating the plate to produce visible colonies of microbes comprising:
   (a) scanning the interaction plate with a scanner which scans a spot in a series of adjacent lines to detect a length of interception Li of the spot with the visible colonies of microbes to produce a measurement of the number and size of visible colonies along a line of intersection of the spot with the track;
   (b) calculating the width of the track of visible colonies of microbes along the line of intersection of the spot with the track from the detected length of interception; and
   (c) calculating the growth ratio GRi for each intersection of the spot with the track of visible colonies of microbes by calculating a ratio of the width of the track for the line of intersection of the spot with the interaction plate and a reference width.

2. A method in accordance with claim 1 further comprising:
   (a) calculating the growth interacting substance potency Pi along the line of intersection of the spot with the track of visible colonies of microbes; and
   (b) plotting the potency Pi versus growth ratio GRi for successive scans of the spot scanner of the interaction plate to produce a growth curve.

3. A method in accordance with claim 1 wherein:
   (a) the track is a spiral with a radial advance $\Delta R$ per revolution of the spiral;
   (b) the interaction plate has a gradient of deposition of the growth interacting substance which decreases in volume per unit length as the radius of the spiral track increases; and
   (c) the microbe containing solution concentration is constant per unit length of the track.

4. A method in accordance with claim 3 wherein the calculation of the width Wi of the track of visible microbe colonies for each scan of the interaction plate is made in accordance with the equation $Wi = \Delta R \times ICi/N$ where $\Delta R$ is the radial advance between successive revolutions of the spiral of the interaction plate, N is the number of clock pulses produced per revolution of the scanner and ICi is equal to the length of interception of the spot along the ith revolution of the scanner.

5. A method in accordance with claim 4 wherein the spot scanner scans in circular patterns which change in radius by the uniform distance $\Delta r$ between successive revolutions of the spot.

6. A method in accordance with claim 4 wherein the spot scanner scans in a spiral pattern of uniformly changing distance $\Delta r$ per revolution of the spot.

7. A method in accordance with claim 3 further comprising:
   (a) detecting the point on the interaction plate where visible microbial growth is inhibited;
   (b) calculating the growth interacting substance potency Pi for the point on the interaction plate where visible microbial growth is inhibited; and
   (c) calculating the growth ratio GRi where visible microbial growth is inhibited.

8. A method in accordance with claim 3 further comprising:
   (a) detecting the point on the interaction plate where the visible microbial growth changes from continuous colonies to discontinuous colonies;
   (b) calculating the growth interacting substance potency Pi for the point where the visible microbial growth changes from continuous to discontinuous; and
   (c) calculating the growth ratio GRi for the point where the visible microbial growth changes from continuous to discontinuous.

9. A method in accordance with claim 3 further comprising analyzing the growth curve to quantitate selected growth curve parameters.

10. A method in accordance with claim 1 wherein the growth interacting substance is a biocide.

11. A method in accordance with claim 1 wherein the growth interacting substance is an antibiotic.

12. A method in accordance with claim 1 wherein the growth interacting substance is a mutagen.

13. An apparatus for measuring the effect of a growth interacting substance on microbial growth by utilizing an interaction plate which contains visible colonies of microbes in a track produced by the programmed deposition of a microbe containing solution in a track on the plate and the programmed deposition of a track of the growth interacting substance on the interaction plate in contact with the microbes and incubating the plate to produce visible colonies of microbes comprising:
   (a) scanning means for scanning a spot in a series of adjacent lines for detecting the visible colonies of microbes along a line of intersection of the spot with the track of visible colonies of microbes;
   (b) means responsive to the scanning means for measuring a length of interception Li of the spot with the visible colonies of microbes to produce a measurement of the number and size of visible colonies along the line of intersection of the track of visible colonies;
   (c) means responsive to the means for measuring a length of interception for calculating the track width Wi of visible colonies of microbes for each line of intersection of the spot with the visible colonies; and
   (d) means for calculating the growth ratio GRi for each line of intersection of the spot with the track of visible colonies of microbes by calculating a ratio of track width for the line of intersection of the spot with the track of visible colonies and a reference width.

14. An apparatus in accordance with the claim 13 further comprising:
   (a) means for calculating the growth interaction substance potency Pi at each line of intersection of the spot with the track of visible colonies of microbes; and
   (b) means for plotting the potency Pi versus growth ratio GRi for successive lines of intersection of the spot with visible colonies.

15. An apparatus in accordance with claim 13 further comprising:
   (a) an interaction plate;
   (b) each track is a spiral with a radial advance $\Delta R$ per revolution of the spiral;
   (c) the interaction plate has a gradient of deposition of the growth interacting substance which decreases in volume per unit length as the radius of the spiral track increases; and
   (d) the microbe containing solution deposited per unit length of the track is constant.

16. An apparatus in accordance with claim 15 wherein the means for calculating average track width Wi solves the equation $Wi = \Delta R \times ICi/N$ where $\Delta R$ is the radial advance between successive revolutions of the spiral of the interaction plate, N is the number of clock pulses produced per revolution of the scanner and ICi is equal to the length of interception of the spot along the ith revolution of the scanner.

17. An apparatus in accordance with claim 16 wherein the scanning means is a circular spot scanner which scans in circular patterns which change in radius by the uniform distance $\Delta r$ between successive lines of the spot.

18. An apparatus in accordance with claim 16 wherein the scanning means is a spiral spot scanner which scans a spot in a uniformly changing radius of distance $\Delta r$ per revolution of the spot.

19. An apparatus in accordance with claim 15 further comprising:
   (a) means for detecting the point on the interaction plate where visible microbial growth is inhibited;
   (b) means for calculating the growth interacting substance potency Pi for the point on the interaction plate where visible microbial growth is inhibited; and
   (c) said means for calculating calculates the growth ratio GRi for the point where the growth of the visible colonies of microbes is inhibited.

20. An apparatus in accordance with claim 15 further comprising:
   (a) means for detecting the point on the interaction plate where the visible colonies of microbes change from continuous colonies to discontinuous colonies;
   (b) means for calculating the growth interacting substance potency Pi for the point where the visible colonies of microbes change from continuous to discontinuous; and
   (c) said means for calculating calculates the growth ratio GRi for the point where the visible colonies of microbes change from continuous to discontinuous.

21. An apparatus in accordance with claim 16 or 17 wherein the means for measuring the length of interception comprises:
   (a) an AND gate having two inputs and an output, the first input being an output signal from the scanning means of the visible colonies of microbes, and the second input signal being clock pulses from scanning means;
   (b) means responsive to clock pulses from the scanning means for signaling the end of scanning of each line; and
   (c) means responsive to the output of the means for signaling the end of scanning of each line and the output of the AND gate for summing the number of clock pulses during which the spot of the scanning means is intersecting visible colonies of microbes during each line of scanning, the means for signaling having an output coupled to the means for calculating the growth ratio GRi.

22. An apparatus in accordance with claim 21 further comprising:
   (a) means for counting the number of the line scan of the scanning means;
   (b) means for calculating the growth ratio GRi having an input coupled to the clock pulses from the scanning means;
   (c) means for calculating the average scan radius Ri for each line of intersection of the spot with the track of visible colonies of microbes, the means for calculating the average scan radius Ri having an input coupled to an output of the means for signaling the end of scanning of each line, an input of the initial scan radius Ro and an input of $\Delta r$ and solving the equation $Ri = (Ro - \frac{1}{2}\Delta r) - i\Delta r$ where i is the number of the line scan of the scanning means and is an output from the means for counting the number of the line scan of the scanning means and $\Delta r$ is the change in radius of the scanner per line scan of the scanning means;
   (d) means for calculating the deposition factor DFi for each line of intersection of the spot with the track of visible colonies of microbes of the interaction plate having inputs of the average scan radius Ri, KD, and n where KD and n are constants of an apparatus used for depositing the spiral track, RA is the distance from the deposition starting radius to the radial position of the point of interest on the spiral track and $DFi = \times 10 \; EXP \; (-n \times RA)$; and
   (e) means for calculating the growth interacting substance potency Pi which is responsive to the means for calculating the deposition fact DFi, the means for calculating the growth potency Pi having inputs RP, h, and SR wherein RP is the reference potency of the growth interacting substance, h is the thickness of the culture medium on the interaction plate and the control plate, if used, and SR is a correction factor to account for incomplete diffusion between adjacent tracks.

* * * * *